(12) United States Patent
Stensrud

(10) Patent No.: US 9,290,509 B2
(45) Date of Patent: Mar. 22, 2016

(54) MONOALLYL, MONOGLYCIDYL ETHERS AND BISGLYCIDYL ETHERS OF ISOHEXIDES

(71) Applicant: ARCHER DANIELS MIDLAND COMPANY, Decatur, IL (US)

(72) Inventor: Kenneth Stensrud, Decatur, IL (US)

(73) Assignee: Archer Daniels Midland Company, Decatur, IL (US)

( * ) Notice: Subject to any disclaimer, the term of this patent is extended or adjusted under 35 U.S.C. 154(b) by 0 days.

(21) Appl. No.: 14/401,143

(22) PCT Filed: Jun. 10, 2013

(86) PCT No.: PCT/US2013/044878
§ 371 (c)(1),
(2) Date: Nov. 14, 2014

(87) PCT Pub. No.: WO2013/188253
PCT Pub. Date: Dec. 19, 2013

(65) Prior Publication Data
US 2015/0141672 A1 May 21, 2015

Related U.S. Application Data

(60) Provisional application No. 61/669,728, filed on Jul. 10, 2012, provisional application No. 61/658,118, filed on Jun. 11, 2012.

(51) Int. Cl.
*C07D 493/04* (2006.01)
(52) U.S. Cl.
CPC .................................. *C07D 493/04* (2013.01)

(58) Field of Classification Search
CPC ..................................................... C07D 493/04
See application file for complete search history.

(56) References Cited

U.S. PATENT DOCUMENTS 4,769,379 A * 9/1988 Leitold et al. ................. 514/290

FOREIGN PATENT DOCUMENTS

JP          2011-213716     * 10/2011  .............. C07C 41/16

OTHER PUBLICATIONS

Rose, M., "Isosorbide as a Renewable Platform chemical for Versatile Applications-Quo Vadis?." ChemSusChem 5.1 (2012): 167-176.*
JP 2011-213716 AIPN Machine Translation Aug. 3, 2015, p. 1-38.*
Chrysanthos, M., "Preparation and properties of bio-based epoxy networks derived from isosorbide diglycidyl ether." Polymer 52.16 (2011): 3611-3620.*
Wright, L. W.,"Catalytic isomerization of polyhydric alcohols. 1 ii. the isomerization of isosorbide to isomannide and isoidide." The Journal of Organic Chemistry 29.10 (1964): 2979-2982.*

* cited by examiner

*Primary Examiner* — Samantha Shterengarts
*Assistant Examiner* — Matt Mauro
(74) *Attorney, Agent, or Firm* — William B. Miller

(57) ABSTRACT

An improved, high yielding process is disclosed for making bisglycidyl ether derivatives of isosorbide, isomannide and/or isoidide, wherein up to quantitative yields overall are demonstrated. In another related aspect, a process is disclosed for making novel monoallyl, monoglycidyl ether derivatives or a combination of monoallyl, monoglycidyl ether derivatives and bisglycidyl ether derivatives via the same diallyl isohexide intermediate.

5 Claims, No Drawings

MONOALLYL, MONOGLYCIDYL ETHERS AND BISGLYCIDYL ETHERS OF ISOHEXIDES

This application is a 35 U.S.C. §371 national phase entry of International Application No. PCT/US2013/044878, filed Jun. 10, 2013, which claims priority from U.S. Provisional Patent Application 61/669,728, filed Jul. 10, 2012.

The present invention relates generally to cyclic bifunctional materials such as are used for monomers in polymer synthesis and as intermediates generally, and to the methods by which such materials are made. More particularly, the invention relates to the mono and bisglycidyl ethers of isohexides and their synthesis.

Bisglycidyl ethers of dihydric compounds are known in the polymer art, for example, the bisglycidyl ethers of dihydric phenolic compounds and of aliphatic glycols containing two primary hydroxyl groups are used in preparing epoxy resins. The isohexides—isosorbide, isomannide, and isoidide—are bicyclic dihydric compounds having fused tetrahydrofuran rings and cis-bound hydroxyl groups in exo-exo, endo-endo and exo-endo stereoconfigurations, and bisglycidyl ethers of these materials have also been synthesized for use as monomers for making epoxy resins, as well as for inhibiting the growth of certain cancerous cells.

In U.S. Pat. No. 3,272,845 to Zech at al., for example, the bisglycidyl ethers of isosorbide, isomannide and isoidide are indicated as having been made by forming a solution of a salt of the particular isohexide by reaction with an alkali metal hydride, then reacting the formed solution with a stoichiometric excess of epichlorohydrin, and recovering the formed bisglycidyl ether from the reaction mixture, col. 1, lines 53-59. Yields, however, were low: 17.6% of theoretical for isosorbide bisglycidyl ether; 14.6% for isomannide bisglycidyl ether; and 16.2% for isoidide bisglycidyl ether. Additionally, Zech at al. reported that their process was developed after conventional methods of forming the glycidyl ethers of hydroxyl compounds—by reaction with epichlorohydrin followed by dehydrohalogenation and by epoxidizing the diallyl ethers of the isohexides with aqueous peracetic acid—had "failed" to produce the desired bisglycidyl ether products.

More recently, in U.S. Pat. No. 4,769,379 to Leitold et al., the monoglycidyl ethers of the isohexides were reported as being made through epoxidizing, for example, 2-allylisosorbide (Examples 1 b, 10b, 13b) or 5-allylisosorbide (Example 5b). In similar manner, monoglycidyl ethers were also made from derivatives of the isohexides via corresponding allyl compounds such as those listed, for example, at column 8, lines 38-57. Bisglycidyl ethers were also made in Example 7 from isosorbide and in Example 12 from isomannide, via the same method used by Zech et al. but also via a different method, wherein a diallyl isosorbide and diallyl isomannide were respectively reacted with 3-chloroperbenzoic acid (alternatively found in the literature as meta-chloroperbenzoic acid).

The '379 patent does not indicate whether the yields provided by the alternative method were improved compared to the former method, and in fact does not indicate what yields were realized by either method. However, in the context of a process for manufacturing the bisglycidyl ethers from an isohexide by means of an allyl or diallyl isohexide intermediate, the examples given would indicate that the overall yields in Leitold et al's process leave considerable room for improvement; thus, for instance, in Example 1a, the yield of 2-allyl isosorbide was calculated at just over 31% of the theoretical yield.

SUMMARY OF THE INVENTION

The present invention in a first aspect concerns an improved, high yielding process for making a bisglycidyl ether of an isohexide (isosorbide, isomannide or isoidide) via a diallyl isohexide intermediate, wherein an isohexide stereoisomer is reacted with a Brønsted base whose conjugate acid has an acid dissociation constant pKa greater than 16 to form a conjugate base of the isohexide stereoisomer, then the conjugate base of the isohexide stereoisomer is reacted with allyl bromide to form the diallyl isohexide derivative. Preferably the diallyl isohexide derivative is realized from this method in substantially a quantitative yield. The diallyl isohexide is combined with at least two mole equivalents of meta-chloroperbenzoic acid to form the bisglycidyl ether, again preferably being produced in substantially a quantitative yield. In a preferred embodiment, the diallyl isohexide is added to the meta-chloroperbenzoic acid in a dropwise or otherwise controlled manner over time.

In a second aspect, the present invention concerns a process for making either or both of mono and bisglycidyl ethers from a diallyl isohexide, wherein a diallyl isohexide is combined with less than two mole equivalents of meta-chloroperbenzoic acid. In a preferred embodiment, the combination is accomplished gradually over time, for example, by adding the diallyl isohexide or isohexides intermediate in a dropwise manner to the meta-chloroperbenzoic acid.

In a third aspect, the present invention concerns novel monoallyl, monoglycidyl ether derivatives of the isohexides corresponding to the structures shown below:

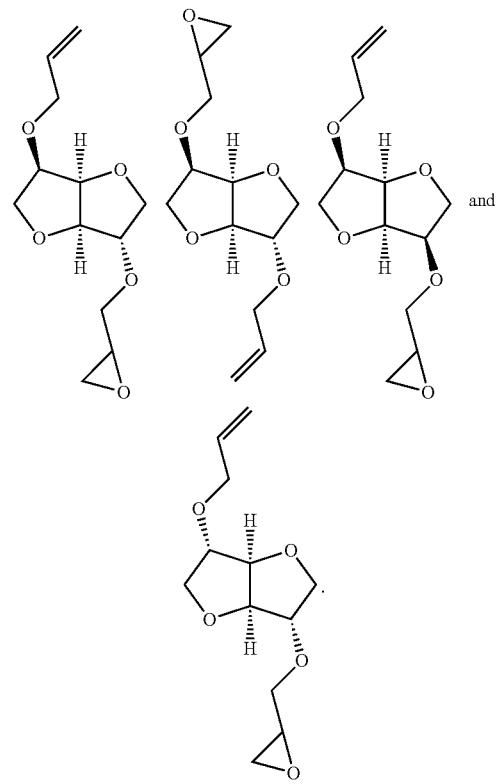

DETAILED DESCRIPTION OF PREFERRED EMBODIMENTS

In a first aspect as just mentioned, the present invention concerns an improved process for making any of the bisglycidyl ethers of isosorbide, isomannide and isoidide, wherein the yields are dramatically improved compared to the known methods for making these materials. Preferably, the overall yields from the starting isohexide, or mixture of isohexides if desired, are at least 90 percent, more preferably are at least 95 percent and most preferably can be substantially a quantitative yield.

In this first aspect, the diallyl isohexide intermediate (or intermediates for a starting feed of mixed isohexides) is first produced as described in commonly-assigned, copending Patent Cooperation Treaty Application Serial No. PCT/US2013/037168, filed Apr. 18, 2013 and claiming priority from U.S. Provisional Patent Application Ser. No. 61/658,118, filed Jun. 11, 2012, for "Diallyl Ethers of Anhydrohexitols and Processes for Making the Same" (hereafter, "the WO'168 Application").

In the WO'168 Application, an isohexide or a mixture of isohexides is reacted in a first step with a Brønsted base whose conjugate acid has an acid dissociation constant $pK_a$ greater than 16. Preferably, the Brønsted base has a $pK_a$ of at least 18. In one embodiment, the Brønsted base is potassium t-butoxide; t-butanol, the conjugate acid of t-butoxide, has a $pK_a$ of about 18.

By using a Brønsted base whose conjugate acid has an acid dissociation constant $pK_a$ greater than 16, for example, a Brønsted base such as potassium t-butoxide, formation of the nucleophilic isohexide anion intermediate (the isoidide intermediate is shown) is thermodynamically favored:

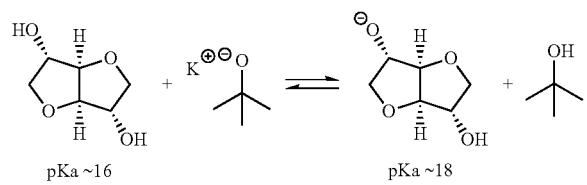

In a second step, this nucleophilic isohexide anion intermediate is reacted with allyl bromide to form the desired diallyl isohexide or isohexides. In this step, t-butoxide is sterically hindered from appreciably reacting with allyl bromide when the same is subsequently added to the isohexide conjugate base(s)/residual potassium butoxide mixture at the temperatures contemplated for the process and made possible by the selection and use of Brønsted bases such as potassium butoxide whose conjugate acids have higher acid dissociation constants.

In a preferred embodiment, the isohexide stereoisomer or stereoisomers and the Brønsted base are reacted in a nonaqueous solvent system, in the substantial absence of water. A preferred nonaqueous solvent is dimethylformamide.

As an additional preferred feature, owing to the ready formation of the conjugate base(s) of the isohexide in the initial combination of the Brønsted base(s) with the isohexide(s), the process is able to be carried out at lower temperatures. For example, in one embodiment, the process is conducted at a reaction temperature of 25 degrees Celsius or less. In another embodiment, the process is conducted at a reaction temperature of 20 degrees Celsius or less. While t-butoxide as noted above is sterically hindered from reacting with the allyl bromide, nevertheless as an additional safeguard against an unwanted side reaction, by carrying out the diallyl isohexide synthesis at lower temperatures the activation barrier to reaction of t-butoxide with allyl bromide will be correspondingly less likely to be surmounted.

In other embodiments, the allyl bromide is added to the conjugate base(s) of the isohexide stereoisomer or stereoisomers gradually over time to reduce the availability of this reagent to react with residual Brønsted base, a less-favored (but still possible) side reaction at these reaction temperatures. In certain embodiments, for example, not more than 13.3% percent allyl bromide is added per minute.

The diallyl isohexide(s) intermediate, as produced by the reaction of an isohexide or mixture of isohexides with the Brønsted base and then by reacting the conjugate base(s) of the isohexide stereoisomer or stereoisomers with allyl bromide as described, is then combined with at least two mole equivalents of meta-chloroperbenzoic acid to form the corresponding bisglycidyl ether or ethers. In preferred embodiments, the combining is accomplished gradually over time given the exothermicity of the epoxidation reaction. Generally, by employing the diallyl isohexide synthesis method of the WO'168 Application, efficiently separating out and recovering the diallyl isohexide or isohexides (for example, also as described in the WO'168 Application) and then reacting the diallyl isohexide intermediate(s) with meta-chloroperbenzoic acid as described herein and as exemplified below, overall process yields can be substantially quantitative.

The isohexide starting material can, as indicated above, be isosorbide, isomannide or isoidide individually or can be a mixture of two or all three of these. Isosorbide is commercially available in industrial and polymer grades, and isomannide is also commercially available. Those skilled in the art will additionally be familiar with methods for making these materials.

Isoidide is not presently made and sold on an industrial scale, but methods for making isoidide have been published. For example, in one embodiment, an isoidide starting material can be prepared by epimerization from isosorbide.

In L. W. Wright, J. D. Brandner, J. Org. Chem., 1964, 29 (10), pp 2979-2982, such epimerization is induced by means of Ni catalysis, using nickel supported on diatomaceous earth. The reaction is conducted under relatively severe conditions, such as a temperature of 220° C. to 240° C. at a pressure of 150 atmosphere. The reaction reaches a steady state after two hours, with an equilibrium mixture containing isoidide (57%), isosorbide (36%) and isomannide (7%). Comparable results were obtained when starting from isoidide or isomannide. Increasing the pH to 10-11 was found to have an accelerating effect, as well as increasing the temperature and nickel catalyst concentration. A similar disclosure is to be found in U.S. Pat. No. 3,023,223.

In EP 1 647 540, L-iditol is prepared starting from sorbitol. In a first step sorbitol is converted by fermentation into L-sorbose, which is subsequently hydrogenated into a mixture of D-sorbitol and L-iditol. This mixture is then converted into a mixture of L-iditol and L-sorbose. After separation from the L-sorbose, the L-iditol can be converted into isoidide. Thus, sorbitol is converted into isoidide in a four-step reaction, in a yield of about 50%.

A preferred method for preparing isoidide by the epimerization of isosorbide is described in European Patent Application No. 12156170.8, "Method of Making Isoidide", filed Feb. 20, 2012, wherein a supported ruthenium catalyst is used at a starting pH of above 7, preferably of from 8 to 10, with the starting pH referring to the pH of the aqueous solution of isosorbide.

The epimerization of isosorbide into isoidide is conducted according to this process under relatively mild conditions, such that an equilibrium production of isoidide can be attained while avoiding mass losses through hydrodeoxygenation and providing a better overall yield compared to the results of Wright and Brandner.

The support can vary widely, including silica, alumina, titania, zirconia, and carbon. A carbon support is preferred, inter alia since it can be operated at a wider pH range than other supports. As well, a carbon supported ruthenium catalyst was observed to act more favorably in the epimerization of isosorbide, than other supports, e.g., $Al_2O_3$. The catalytically active metal preferably consists essentially of ruthenium, and the support preferably consists essentially of carbon. A suitable ruthenium content is described as from 1% to 10% by weight of ruthenium, based on the total weight of the catalyst, preferably being about 5% by weight of the catalyst.

In order to conduct the epimerization, isosorbide is provided in the form of an aqueous solution. The concentration of isosorbide therein may widely vary. However, for the sake of process economics as well as results in terms of yield, it is preferred for the isosorbide concentration to be in a range of from 25% by weight to 75% by weight. More preferably, the isosorbide concentration is 30% to 60% by weight. The optimum concentration is believed to approximately 50% by weight.

The aqueous solution is subjected to an atmosphere comprising hydrogen. The hydrogen pressure can widely vary, for example, from 20 to 200 bars. However, it was found particularly effective to employ a relatively low pressure in the range of from 20 to 55 bars, and preferably about 40 bars.

Calculated on the basis of a water paste comprising 50% of a 5% ruthenium on carbon catalyst, the catalyst concentration in the reactor, calculated as a weight percentage based on the aqueous solution of isosorbide, can range from as low as, e.g., 1% to as high as, e.g. 50%. However, for the sake of process economics as well as results in terms of yield and specificity, it is preferred for a 5% ruthenium catalyst to be employed in a concentration of from 2 to 20%, and more preferably about 4%. It will be understood that these percentages will hold, mutatis mutandis, for other water paste concentrations than 50%, and other catalyst loadings than 5%.

The skilled person will be aware of how to generally conduct the ruthenium catalyzed reaction. Background references in this respect include U.S. Pat. No. 6,177,598 and U.S. Pat. No. 6,570,043.

The ruthenium catalyst as mentioned preferably comprises a carbon support. Different types of carbon support are applicable, e.g. activated carbon or carbon nanotubes. The activated carbon can be, e.g., 50-70% wetted powder. Typically preferred catalysts include commercial ruthenium on carbon catalysts ex BASF or Evonik (Strem Chemicals). A background reference on Ru/C catalysts is Sifontes Herrera et al, J. Chem Technol Biotechnol (2011), "Sugar hydrogenation over a Ru/C catalyst."

The epimerization reaction is conducted preferably at an elevated temperature, i.e. above 20° C., and preferably below 250°. A preferred temperature range is 200° to 240°, most preferably about 220° C. The duration of the reaction will, as the skilled person knows, generally be shorter at higher temperatures. The residence time in the reactor where the isosorbide solution is subjected to hydrogen under the influence of the catalyst, will generally range from 0.1 to 10 hours, preferably. 0.25 to 4 hours, and more preferably 1-2 hours.

It is preferred to adjust the pH of the aqueous solution of isosorbide. Although, for the sake of conducting the epimerization per se, the pH may widely vary, it has been found that unwanted side reactions, which lead to loss of matter as a result of the formation of volatiles, can be reduced considerably by adjusting the pH to a value of 8 to 10.

From the equilibrium mixture, the isoidide starting material can be recovered by separation methods known to the skilled person, such as by chromatographic techniques, selective crystallization or distillation. The latter can be conducted, e.g. as disclosed by Wright et al. J. Org. Chem., 1964, 29 (10), pp 2979-2982, mentioned above. Other references descriptive of methods for separating an epimerization mixture of isosorbide, isomannide and isoidide include commonly-assigned U.S. Pat. No. 7,439,352 and U.S. Pat. No. 6,849,748 to Moore et al, both of which are hereby incorporated herein by reference, as well as U.S. Pat. No. 6,670,033 to Hubbard et al., U.S. Pat. No. 4,564,692 to Feldman et al., U.S. Pat. No. 7,122,661 to Fleche at al. and U.S. Pat. No. 8,008,477 to Fuertes.

In a second aspect, the present invention concerns a process for making either or both of mono and bisglycidyl ethers from a diallyl isohexide, wherein a diallyl isohexide is combined with less than two mole equivalents of meta-chloroperbenzoic acid. In a preferred embodiment, the combination is accomplished gradually over time, for example, by adding the diallyl isohexide or isohexides intermediate in a dropwise manner to the meta-chloroperbenzoic acid.

We have found in this regard that by using less than the two mole equivalents of the meta-chloroperbenzoic acid required to fully oxidize the allyl moieties on the diallyl isohexide(s), novel monoallyl, monoglycidyl ether derivatives of isosorbide, isomannide and isoidide may be made:

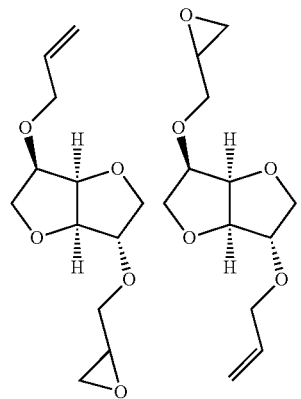

Isosorbide monoallyl, monoglycidyl ether isomers

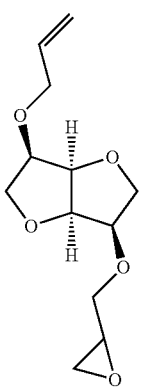 [SMILES: C=CCO[C@@H]1CO[C@H]2[C@@H]1OC[C@H]2OCC1CO1]

Isomannide monoallyl, monoglycidyl ether

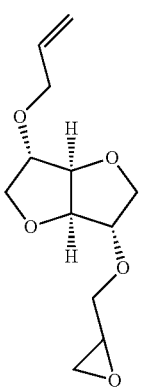 [SMILES: C=CCO[C@H]1CO[C@H]2[C@@H]1OC[C@@H]2OCC1CO1]

Isoidide monoallyl, monoglycidyl ether

Because the double bonds of the allyl moieties are well removed from the bisfuran ring system characteristic of each of the isohexides, it would be expected that any given allyl moiety of a particular diallyl isohexide will oxidize no more or less readily than the other allyl moiety, so that the full spectrum of monoallyl, monoglycidyl ether materials should be possible. As well, the monoallyl, monoglycidyl ether derivatives may be made selectively in comparison to the bisglycidyl ether derivatives by employing closer to one mole equivalent of the meta-chloroperbenzoic acid, for example, 1.1 to 1.2 mole equivalents of meta-chloroperbenzoic acid, and likewise the relative proportion of monoallyl, monoglycidyl ether product to the bisglycidyl ether product can be established as desired by using a corresponding fraction of mole equivalents between one and two mole equivalents of m-CPBA.

Further, by using diallyl isohexide synthesis of the WO'168 Application, quantitative yields of the monoallyl, monoglycidyl ether isohexide derivatives, of the bisglycidyl ether isohexide derivatives or of a desired combination of the monoallyl, monoglycidyl ether and bisglycidyl ether derivatives can be achieved through using a corresponding fraction of mole equivalents between one and two mole equivalents of m-CPBA and carrying out the process otherwise as described above.

The present invention is further illustrated by the following examples:

Example 1

A 2-neck, 100 mL round-bottomed flask was equipped with an argon line and a septum, then charged with 2.28 g of meta-chloroperbenzoic acid (mCPBA, 10.2 mmol) and 20 mL of methylene chloride, then cooled to about 0 degrees Celsius in an ice/saline bath. A separate 50 mL round bottomed flask was charged with 1.00 g of diallylisoidide (4.4 mmol) and 20 mL of methylene chloride, then, upon complete dissolution of the diallylisoidide, the solution was pulled into a 25 cc syringe and added dropwise to the mCPBA solution through the septum of the 2-neck flask, while maintaining 0 deg. C and an argon atmosphere. After being added gradually over a span of about 10 minutes, the solution was allowed to warm to room temperature and the reaction continued for 20 hours. After this time, the solution is observed to contain a profusion of white solid. This solid material was removed through a bed of Celite® diatomaceous earth (about 10 grams), the mother liquor filtrate was then cooled to 0 degrees Celsius in a saline bath. Two successive 50 mL volumes of 10% sodium bisulfate solution were added to remove excess mCPBA, with each step entailing extraction of the bottom, organic phase. The organic phase was then subjected to two successive 50 mL volumes of concentrated sodium bicarbonate, with extraction of the organic phase after each addition. The treated mother liquor was dried with anhydrous magnesium sulfate, then concentrated in vacuo, producing a light yellow, loose oil (1.07 g, 94%, diastereomers). Spectroscopic validation: 1H NMR (CDCl3, 400 MHz), δ (ppm) 4.60 (d, J=6.2 Hz, 2H), 4.00 (s, 2H), 3.86-3.80 (m, 4H), 3.43-3.41 (m, 4H), 3.12 (dd, J=5.0, J=1.6 Hz, 2H), 2.78 (d, J=4.8 Hz, 2H), 2.59 (d, J=4.2 Hz, 2H); 13C (CDCl3, 100 MHz), δ (ppm) 85.59, 84.25, 72.49, 70.46, 53.63, 50.83, 44.56; HRMS (GC-TOF): Calculated for C12H18O6 (m/z), 258.2677. Found (m/z): 258.2691. (Calculated yield furnished above (1.07 g, 94%); Theoretical Yield: 1.11 g.

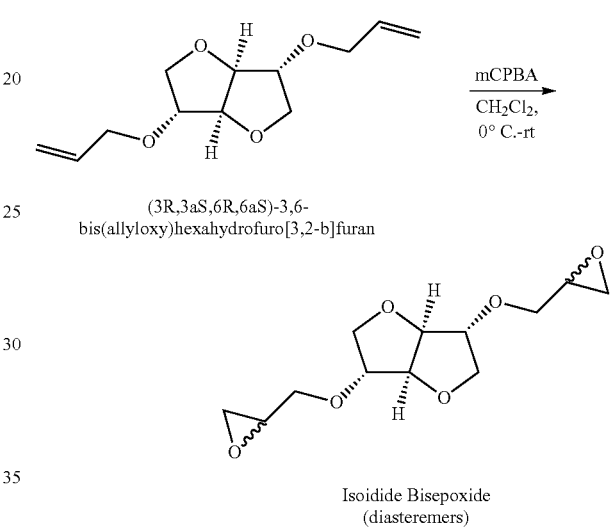

Example 2

An oven dried, two neck round bottomed flask equipped with a Teflon magnetic stir bar was charged with 3.00 g of isoidide (20.5 mmol), 5.30 g potassium t-butoxide (47.2 mmol), and 50 mL of anhydrous dimethylformamide (DMF). This heterogeneous mixture was stirred for 30 minutes at room temperature, then brought to about 0 degrees Celsius in an ice/saturated brine bath. While stirring and under argon, 3.90 mL of allyl bromide (45.2 mmol) was added dropwise via syringe. After addition was complete, the ice bath was removed and the solution warmed to room temperature. The reaction was continued for 4 hours at room temperature under argon. After this time, the heterogeneous solution was filtered to remove potassium bromide and other solids. The filtrate was then transferred to a 250 mL boiling flask containing a Teflon stir bar, was diluted with 50 mL of methylene chloride and 50 mL of water, and vigorously stirred. The biphasic solution was poured into a 250 mL separatory funnel and the bottom organic layer removed into a 125 mL Erlenmeyer flask. This solution was then diluted with another 50 mL volume of water, and the resultant biphasic solution mixed as before. The organic phase was extracted, dried with anhydrous magnesium sulfate and concentrated in vacuo, producing a light yellow oil, 4.46 g (96% yield). GC/MS (EI), one signal m/z 226.1. This corresponds to (3S,3aR,6S,6aR)-3,6-bis(allyloxy)hexahydrofuro[3,2-b]furan (compound B, diallyl isoidide).

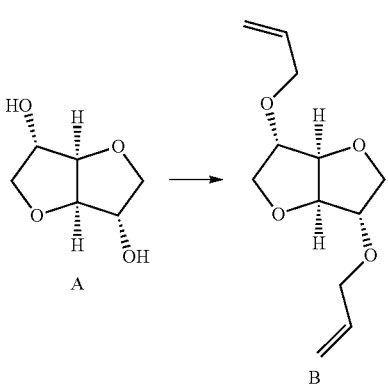

Subsequently, a separate two neck, boiling flask equipped with a Teflon stir bar was charged with 5.44 g of 77% meta-chloroperbenzoic acid (mCPBA, 24.3 mmol) and 30 mL of methylene chloride. After complete dissolution of the mCPBA, the flask was outfitted with a rubber septum and argon line, and immersed in an ice/brine bath at about 0 degrees Celsius. While stirring, under argon, and low-temperature maintenance, 4.40 g (19.4 mmol) of diallyl isoidide (B), previously diluted with 10 mL of methylene chloride, was injected dropwise through the septum via a syringe. Once the diallyl isoidide was completely added, the ice bath was removed and the reaction continued overnight at room temperature. After this time, profuse precipitate was observed and filtered, and the mother liquor was diluted with 50 mL of saturated sodium metabisulfite. This biphasic solution was stirred for 10 minutes, and the organic layer was extracted, then diluted with a saturated solution of sodium bicarbonate. Substantial effervescence was observed (indicating carbon dioxide evolution). The organic layer was then removed, dried with anhydrous magnesium sulfate, and evaporated to dryness, resulting in a light yellow oil, (4.87 g). TLC (2:1 hexanes/ethyl acetate, cerium molybdate stain) manifested three spots, rf1 (B) 0.57, rf2 (D) 0.46, rf3 (C) 0.33. The patent difference in rf would allow facile isolation of B, C and D by silica gel flash chromatography, for example. GC/MS (EI, M+) manifested three signals with m/z consistent with diallyl isoidide (B, 226.1), (3S,3aR,6S,6aR)-3-(allyloxy)-6-(oxiran-2-ylmethoxy)hexahydrofuro[3,2-b]furan (D, 242.0) and (3S,3aR,6S,6aR)-3,6-bis(oxiran-2-ylmethoxy)hexahydrofuro[3,2-b]furan (C, 258.1). The corresponding integration of the signals suggests an approximate 0.5:1:0.5 molar ratio of B:D:C in the product mixture.

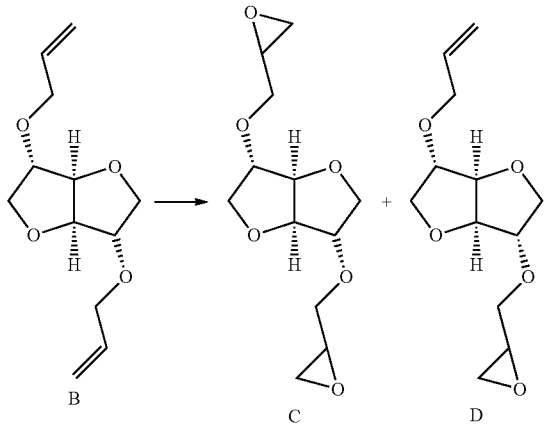

Example 3

An oven dried, two neck round bottomed flask equipped with a Teflon magnetic stir bar was charged with 3.00 g of isosorbide (20.5 mmol), 5.30 g potassium t-butoxide (47.2 mmol), and 50 mL of anhydrous DMF. This heterogeneous mixture was stirred for 30 minutes at room temperature, then brought to about 0 degrees Celsius in an ice/saturated brine bath. While stirring and under argon, 3.90 mL of allyl bromide (45.2 mmol) was added dropwise via syringe. After addition was complete, the ice bath was removed and the solution warmed to room temperature. The reaction was continued for 4 hours at room temperature under argon. After this time, the heterogeneous solution was filtered to remove potassium bromide and other solids. The filtrate was then transferred to a 250 mL boiling flask containing a Teflon stir bar, was diluted with 50 mL of methylene chloride and 50 mL of water, and vigorously stirred. The biphasic solution was poured into a 250 mL separatory funnel and the bottom organic layer removed into a 125 mL Erlenmeyer flask. This solution was then diluted with another 50 mL volume of water, the resultant biphasic solution mixed as before, and the organic phase was extracted, dried with anhydrous magnesium sulfate and concentrated in vacuo, producing a light yellow oil, 4.12 g (89%). This material was spectroscopically confirmed by GC/MS (EI), providing one signal (m/z 226.1) corresponding to (3R,3aR,6S,6aR)-3,6-bis(allyloxy)hexahydrofuro[3,2-b]furan (diallyl isosorbide, B).

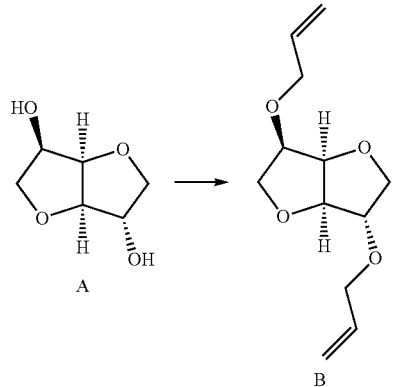

Subsequently, a separate two neck, boiling flask equipped with a Teflon stir bar was charged with 4.34 g of 77% meta-chloroperbenzoic acid (mCPBA, 19.4 mmol) and 30 mL of methylene chloride. After complete dissolution, the flask was outfitted with a rubber septum and argon line, and immersed in an ice/brine bath (about 0 degrees C.). While stirring, under argon, and low-temperature maintenance, 3.51 g (15.5 mmol) of diallyl isosorbide, previously diluted with 10 mL of methylene chloride, was injected dropwise through the septum via a syringe. Once completely added, the ice bath was removed and the reaction proceeded overnight at room temperature. After this time, profuse precipitate was observed and filtered, and the mother liquor was diluted with 50 mL of saturated sodium metabisulfite. This biphasic solution was stirred for 10 minutes, and the organic layer extracted, then diluted with a saturated solution of sodium bicarbonate. Substantial effervescence was observed (indicating CO2 evolution). The organic layer was then removed, dried with anhydrous magnesium sulfate, and evaporated to dryness, resulting in a light yellow oil, (3.66 g). TLC (2:1 Hexanes/Ethyl Acetate, cerium molybdate stain) manifested three spots, ill (B) 0.61, rf2 (D)

0.49, rf3 (C) 0.37. The patent difference in rf would allow facile isolation of B, C and D by silica gel flash chromatography, for example. Spectroscopic analysis by GC/MS (EI, M+) manifested four signals with m/z consistent with the diallyl isosorbide (226.1), (3R,3aR,6S,6aR)-3-(allyloxy)-6-(oxiran-2-ylmethoxy)hexahydrofuro[3,2-b]furan (compound D, 242.0) and 3R,3aR,6S,6aR)-3,6-bis(oxiran-2-ylmethoxy)hexahydrofuro[3,2-b]furan (compound C, 258.1). The corresponding integration of the signals suggests an approximate 0.5:1:0.5 molar ratio of B:D:C in the product mixture.

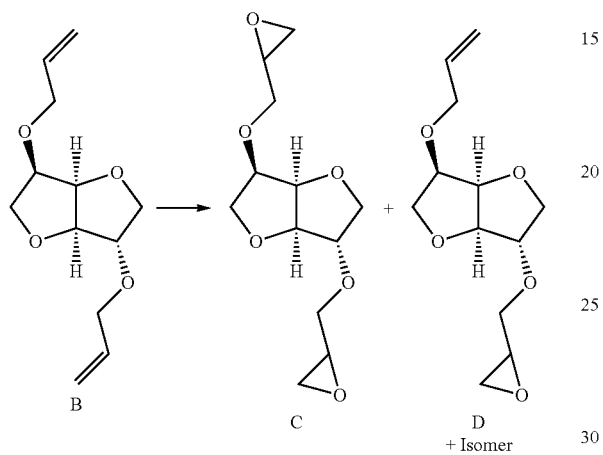

Example 4

An oven dried, two neck round bottomed flask equipped with a Teflon magnetic stir bar was charged with 1.00 g of isomannide (6.84 mmol), 1.69 g potassium t-butoxide (15.1 mmol), and 25 mL of anhydrous DMF. This heterogeneous mixture was stirred for 30 minutes at room temperature, then brought to about 0° C. in an ice/saturated brine bath. While stirring and under argon, 1.30 mL of allyl bromide (15.1 mmol) was added dropwise via syringe. After addition was complete, the ice bath was removed and the solution warmed to room temperature. The reaction continued overnight at room temperature under argon. After this time, the heterogeneous solution was filtered to remove potassium bromide and other solids. The filtrate was then transferred to a 250 mL boiling flask containing a Teflon stir bar, diluted with 50 mL of methylene chloride and 50 mL of water, and vigorously stirred. The biphasic solution was poured into a 250 mL separatory funnel and the bottom organic layer removed into a 125 mL Erlenmeyer flask. This solution was then diluted with another 50 mL volume of water. The resultant biphasic solution was mixed as before, and the organic phase was extracted, dried with anhydrous magnesium sulfate and concentrated in vacuo, producing a light yellow oil, 1.42 (91%). Spectroscopic analysis confirmed diallyl isomannide: 1H NMR (400 MHz, CDCl$_3$) δ (ppm) 5.93-5.91 (m, 2H), 5.27 (d, J=8.2 Hz, 2H), 5.19 (d, J=8.0 Hz, 2H), 4.52 (s, 2H), 4.13 (dd, J=6.2 Hz, J=1.8 Hz, 2H), 4.1 (m, 4H), 3.88 (d, J=7.2 Hz, 2H), 3.70 (d, J=7.0 Hz, 2H); $^{13}$C NMR (125 MHz, CDCl$_3$) δ (ppm) 134.73, 117.98, 80.63, 79.89, 71.92, 71.26; GC/MS (EI) one signal m/z 226.1, corresponds to diallyl isomannide ((3R, 3aR,6R,6aR)-3,6-bis(allyloxy)hexahydrofuro[3,2-b]furan, compound B).

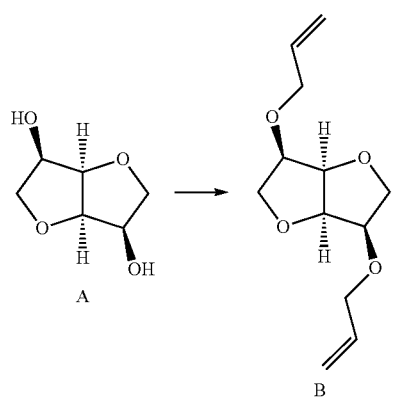

Separately, a two neck, boiling flask equipped with a Teflon stir bar was charged with 1.56 g of 77% meta-chloroperbenzoic acid (mCPBA, 6.97 mmol) and 20 mL of methylene chloride. After complete dissolution, the flask was outfitted with a rubber septum and argon line, and immersed in an ice/brine bath at about 0 degrees Celsius. While stirring under argon and low-temperature maintenance, 900 mg of diallyl isomannide, previously diluted with 10 mL of methylene chloride, was injected dropwise through the septum via a syringe. Once completely added, the ice bath was removed and the reaction proceeded overnight at room temperature. After this time, profuse precipitate was observed. The precipitate was filtered, and the mother liquor diluted with 50 mL of saturated sodium metabisulfite. This biphasic solution was stirred for 10 minutes, and the organic layer was extracted then diluted with a saturated solution of sodium bicarbonate. Substantial effervescence was observed (indicating CO2 evolution). The organic layer was then removed, dried with anhydrous magnesium sulfate, and evaporated to dryness, resulting in a light yellow oil, (947 mg). TLC (2:1 Hexanes/Ethyl Acetate, cerium molybdate stain) manifested two spots only, ill (D) 0.52, rf2 (C) 0.32. The sizeable disparity in rf values would permit facile sequestration of C and D by silica gel flash chromatography, for example. GC/MS (EI, M+) manifested two signals with m/z consistent with (3R,3aR,6R, 6aR)-3,6-bis(oxiran-2-ylmethoxy)hexahydrofuro[3,2-b]furan, compound C (242.0) and with (3R,3aR,6R,6aR)-3-(allyloxy)-6-(oxiran-2-ylmethoxy)hexahydrofuro[3,2-b]furan, compound D (258.1). The corresponding integration of the signals suggests an approximate 3:1 molar ratio of C to D in the product mixture. 1H NMR (400 MHz, CDCl3) revealed signals that accorded to C and D only; peak integration was congruent to GC/MS in suggesting a 3:1 molar ratio of C to D in the mixture.

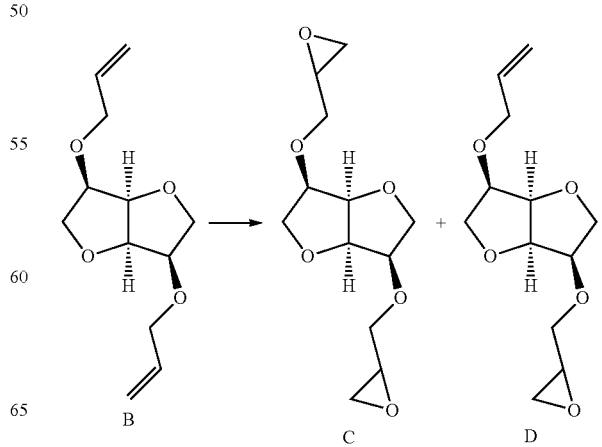

The invention claimed is:

1. A process for making a bisglycidyl ether of an isohexide, comprising the steps of
forming a diallyl isohexide intermediate, by first forming a conjugate base of an isohexide stereoisomer through reacting the isohexide stereoisomer with a Brønsted base whose conjugate acid has an acid dissociation constant pKa greater than 16 in a nonaqueous solvent system and at a temperature of 25 degrees Celsius or less, then reacting the conjugate base of the isohexide stereoisomer with allyl bromide added gradually at a rate of not more than 13.3 percent per minute to form the diallyl isohexide intermediate; and
reacting the diallyl isohexide intermediate with at least two mole equivalents of meta-chloroperbenzoic acid, wherein the diallyl isohexide intermediate is added to the meta-chloroperbenzoic acid in a controlled manner over a period of time.

2. The process as in claim 1, wherein the bisglycidyl ether of isohexide is produced at an overall yield of at least 95 percent based on the amount of the starting isohexide.

3. The process as in claim 1, wherein the Brønsted base has a pKa of at least 18.

4. The process as in claim 3, wherein the Brønsted base is potassium t-butoxide.

5. A process for making a monoallyl, monoglycidyl ether derivative of an isohexide, comprising;
forming a diallyl isohexide intermediate, by first forming a conjugate base of an isohexide stereoisomer through reacting the isohexide stereoisomer with a Brønsted base whose conjugate acid has an acid dissociation constant pKa greater than 16 in a nonaqueous solvent system and at a temperature of 25 degrees Celsius or less, then reacting the conjugate base of the isohexide stereoisomer with allyl bromide added gradually at a rate of not more than 13.3 percent per minute to form the diallyl isohexide intermediate; and
reacting the diallyl isohexide intermediate with less than two mole equivalents of meta-chloroperbenzoic acid, wherein the diallyl isohexide intermediate is added to the meta-chloroperbenzoic acid in a controlled manner over a period of time.

* * * * *